(12) United States Patent
Inosaka et al.

(10) Patent No.: US 8,092,827 B2
(45) Date of Patent: Jan. 10, 2012

(54) MEDICAL NON-CROSSLINKED PRESSURE-SENSITIVE ADHESIVE COMPOSITION, MEDICAL ADHESIVE SHEET EMPLOYING THE SAME, AND PROCESS FOR PRODUCING MEDICAL NON-CROSSLINKED PRESSURE-SENSITIVE ADHESIVE COMPOSITION

(75) Inventors: Keigo Inosaka, Ibaraki (JP); Takateru Muraoka, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 2143 days.

(21) Appl. No.: 11/113,969

(22) Filed: Apr. 26, 2005

(65) Prior Publication Data

US 2005/0238703 A1 Oct. 27, 2005

(30) Foreign Application Priority Data

Apr. 27, 2004 (JP) ................. P2004-131809

(51) Int. Cl.
*A61F 13/02* (2006.01)
*A61L 15/16* (2006.01)
(52) U.S. Cl. ............... 424/448; 424/449; 424/484
(58) Field of Classification Search .......... 424/448, 424/449, 484
See application file for complete search history.

(56) References Cited

U.S. PATENT DOCUMENTS 4,370,380 A 1/1983 Shah
6,146,656 A * 11/2000 Hori et al. ............. 424/448

FOREIGN PATENT DOCUMENTS

| JP | 7-69871 A | 3/1995 |
|----|-----------|--------|
| JP | 2000-26285 A | 1/2000 |
| JP | 2002-212064 A | 7/2002 |

OTHER PUBLICATIONS

Patent Abstracts of Japan—(JP-A-2000 026285) Inoue Yuichi, "Plaster" (2000) vol. 2000, No. 4.
Patent Abstracts of Japan—(JP-A-2002 212064) Obara Minoru, "Base for Cosmetic and Medicinal Application Agent" (2002), vol. 2002, No. 11.
Patent Abstracts of Japan—(JP-A-07 069871) Asai Masaharu, "Base for External Tape Agent and External Tape Agent Using the Same Base" (1995), vol. 1995, No. 6.
European Search Report dated Aug. 12, 2005.

* cited by examiner

*Primary Examiner* — Michael G Hartley
*Assistant Examiner* — Micha-Paul Young
(74) *Attorney, Agent, or Firm* — Sughrue Mion, PLLC

(57) ABSTRACT

A medical non-crosslinked pressure-sensitive adhesive composition which not only has relatively high resistance to water during perspiration or the like and shows a sufficient skin adhesive force, but also can contain a large amount of a liquid plasticizer and hence have reduced skin-irritating properties. These compositions comprise an adhesive polymer A having a weight-average molecular weight of 500,000-1,000,000, an adhesive polymer B having a weight-average molecular weight of 1,000,000-1,500,000, and a liquid plasticizer, wherein the adhesive polymer A is a polymer obtained by copolymerizing one or more alkyl (meth)acrylates with N-vinyl-2-pyrrolidone and the adhesive polymer B is either a polymer obtained by the polymerization of one or more alkyl (meth)acrylates or a polymer obtained by copolymerizing one or more alkyl (meth)acrylates with one or more comonomers other than N-vinyl-2-pyrrolidone. Also provided are a medical adhesive sheet and a process for producing the medical non-crosslinked pressure-sensitive adhesive composition.

10 Claims, No Drawings

MEDICAL NON-CROSSLINKED PRESSURE-SENSITIVE ADHESIVE COMPOSITION, MEDICAL ADHESIVE SHEET EMPLOYING THE SAME, AND PROCESS FOR PRODUCING MEDICAL NON-CROSSLINKED PRESSURE-SENSITIVE ADHESIVE COMPOSITION

FIELD OF THE INVENTION

The present invention relates to a medical non-crosslinked pressure-sensitive adhesive composition suitable for use as a pressure-sensitive adhesive composition for medical preparations to be applied to the skin, such as dressing materials, surgical tapes, and adhesive sheets containing a percutaneously absorbable drug. The present invention further relates to a medical adhesive sheet employing the adhesive and to a process for producing the medical non-crosslinked pressure-sensitive adhesive composition.

BACKGROUND OF THE INVENTION

Adhesive sheets are used in a wide range of situations in medical fields. Examples thereof include dressing materials and sticking plasters for use in protecting damaged skin surface such as wounded parts and bedsore parts, surgical tapes for use in fixing a catheter, gauze, or the like to a skin surface, and adhesive sheets for transdermal administration of a drug into the body through the skin.

In the case where these medical adhesive sheets are to be applied directly to the skin surface and used in this state, the pressure-sensitive adhesive compositions to be used therein are required to exhibit a skin adhesive force which prevents the adhesive sheets from peeling off even when the underlying skin part moves or perspires in some degree.

On the other hand, when a pressure-sensitive adhesive composition having a too high skin adhesive force is used, there are cases where stripping the medical adhesive sheet off the skin surface not only pulls the underlying skin part to cause an unnecessary pain to the user but also physically strips off the horny layer of the skin to irritate the skin.

Consequently, in the development of a medical adhesive sheet, it is highly important for the pressure-sensitive adhesive composition to reconcile the sufficient retention of a skin adhesive force with reduced skin-irritating properties while attaining a good balance between them.

A technique for regulating these properties has been investigated which comprises conducting a crosslinking treatment, such as a chemical crosslinking treatment using a crosslinking agent or a physical crosslinking treatment using electron beams or ultraviolet, to thereby increase the cohesive force of the pressure-sensitive adhesive layer and incorporating a large amount of a liquid plasticizer into the pressure-sensitive adhesive layer to thereby moderately reduce the skin adhesive force thereof (see, for example, document 1).

However, there are cases where compounds having a functional group, e.g., a percutaneously absorbable drug and an antioxidant, should be incorporated into some medical pressure-sensitive adhesive compositions, and the crosslinking treatment of pressure-sensitive adhesive compositions containing such compounds may cause the following problems.

When a pressure-sensitive adhesive composition to be subjected to a chemical crosslinking treatment contains compounds having a functional group, there are cases where the crosslinking agent reacts with the functional groups of these compounds and, as a result, the effects which in themselves are produced by these compounds, such as a pharmacological effect and an oxidation inhibitive effect, are not produced.

Also, there are cases where the crosslinking agent is consumed by those reactions and the adhesive polymer serving as the basic component of the pressure-sensitive adhesive layer is not sufficiently crosslinked and the cohesive force of the pressure-sensitive adhesive layer does not improve.

In the case of a physical crosslinking treatment, the treatment with electron beams, ultraviolet, or the like for crosslinking may decompose or alter the compounds having a functional group to cause the same problems as in the chemical crosslinking treatment.

Those problems are remarkable especially when the pressure-sensitive adhesive composition contains a percutaneously absorbable drug. This is because most percutaneously absorbable drugs have some functional group in the molecule to exhibit physiological activity.

Various techniques for eliminating those problems have been investigated which comprise incorporating a large amount of a liquid plasticizer into a pressure-sensitive adhesive composition without conducting a crosslinking treatment. Examples of such techniques which have been proposed include a technique in which a pressure-sensitive adhesive composition comprising a methyl vinyl ether/maleic anhydride copolymer having a viscosity in a specific range and a liquid compound having plasticizing action and/or absorption-accelerating action is used (see, for example, document 2) and a technique in which an adhesive polymer having an extremely high weight-average molecular weight is used and both a liquid plasticizer and a solid plasticizer are incorporated therein (see, for example, document 3).

However, the former technique has the following disadvantage. Since a methyl vinyl ether/maleic anhydride copolymer, which is a water-soluble polymer, is used as an adhesive polymer, the pressure-sensitive adhesive layer, during wear, absorbs water such as the sweat of the skin and comes to have a reduced cohesive force. There are cases where stripping off the adhesive sheet after use results in the so-called adhesive remaining on the skin.

On the other hand, in the latter technique, the decrease in cohesive force caused by water absorption described above can be diminished in some degree by selecting a water-insoluble adhesive polymer. However, when a liquid plasticizer is incorporated in an amount exceeding 100 parts by weight per 100 parts by weight of the adhesive polymer, there are cases where the liquid plasticizer and other ingredients cannot be held in the pressure-sensitive adhesive layer.

Although techniques for reducing skin-irritating properties by incorporating a large amount of a liquid plasticizer into a non-crosslinked pressure-sensitive adhesive composition have been known as described above, these are still unsatisfactory. A further improvement is desired.

Document 1: JP-A-2002-212064 (claim 1)
Document 2: JP-A-7-69871 (claim 1)
Document 3: JP-A-2000-26285 (claim 1)

SUMMARY OF THE INVENTION

The present invention was achieved in order to overcome the above-described problems in the medical non-crosslinked pressure-sensitive adhesive compositions proposed hitherto. An object of the present invention is to provide a medical non-crosslinked pressure-sensitive adhesive composition which not only has relatively high resistance to water during, e.g., perspiration and retains a sufficient skin adhesive force, but also can contain a large amount of a liquid plasticizer and hence have reduced skin-irritating properties.

Another object of the present invention is to provide a medical adhesive sheet employing the medical non-crosslinked pressure-sensitive adhesive composition.

A still other object of the present invention is to provide a process for producing the medical non-crosslinked pressure-sensitive adhesive composition.

Namely, the present invention relates to a medical non-crosslinked pressure-sensitive adhesive composition which comprises an adhesive polymer A having a weight-average molecular weight of from 500,000 to 1,000,000, an adhesive polymer B having a weight-average molecular weight of from 1,000,000 to 1,500,000, and a liquid plasticizer, wherein the adhesive polymer A is a polymer obtained by copolymerizing one or more alkyl (meth)acrylates with N-vinyl-2-pyrrolidone and the adhesive polymer B is either a polymer obtained by the polymerization of one or more alkyl (meth)acrylates or a polymer obtained by copolymerizing one or more alkyl (meth)acrylates with one or more comonomers other than N-vinyl-2-pyrrolidone.

The present invention further relates to a medical adhesive sheet which comprises a support and, formed on at least one side of the support, a layer of the medical non-crosslinked pressure-sensitive adhesive composition described above.

The present invention furthermore relates to a process for producing a medical non-crosslinked pressure-sensitive adhesive composition which comprises:

(a) polymerizing one or more alkyl (meth)acrylates by the emulsion polymerization method or copolymerizing one or more alkyl (meth)acrylates with one or more comonomers other than N-vinyl-2-pyrrolidone by the emulsion polymerization method to prepare a liquid containing a polymer having a weight-average molecular weight of from 1,000,000 to 1,500,000 as an adhesive polymer B;

(b) mixing a liquid plasticizer is mixed with the liquid prepared in (a) to thereby swell the adhesive polymer B; and (c) mixing the liquid prepared in (b) with a liquid which contains an adhesive polymer A having a weight-average molecular weight of from 500,000 to 1,000,000 and has been separately prepared by copolymerizing one or more alkyl (meth)acrylates with N-vinyl-2-pyrrolidone by the solution polymerization method.

The medical non-crosslinked pressure-sensitive adhesive composition of the present invention exhibits an extremely high cohesive force even without undergoing a crosslinking treatment, because two adhesive polymers each having a specific monomer composition and a specific weight-average molecular weight are used therein in combination.

As a result, even when the pressure-sensitive adhesive composition contains a liquid plasticizer in an amount exceeding 100 parts by weight per 100 parts by weight of the adhesive polymers, it exhibits a skin adhesive force which enables the adhesive to be sufficiently usable in medical adhesive sheets. In addition, the pressure-sensitive adhesive composition has reduced skin-irritating properties due to the liquid plasticizer incorporated in a large amount.

Furthermore, the medical non-crosslinked pressure-sensitive adhesive composition of the present invention is not subjected to a crosslinking treatment. Thus, even when it contains compounds having a functional group (e.g., a percutaneously absorbable drug, antioxidant, and antibacterial), these compounds are less apt to decompose or alter and can sufficiently exhibit their performances.

Thus, the present invention can provide an excellent medical non-crosslinked pressure-sensitive adhesive composition capable of reconciling a sufficient skin adhesive force and low skin-irritating properties while attaining a good balance between these, and further provide a medical adhesive sheet employing the adhesive composition.

In the process of the present invention for producing the medical non-crosslinked pressure-sensitive adhesive composition, an adhesive polymer B prepared by emulsion polymerization is swollen with a liquid plasticizer and then mixed with an adhesive polymer A separately prepared by solution polymerization. Because of this operation, the liquid containing the adhesive polymer B and prepared through emulsion polymerization in an aqueous medium can be homogeneously mixed easily with the liquid containing the adhesive polymer A and prepared through solution polymerization.

DETAILED DESCRIPTION OF THE INVENTION

The medical non-crosslinked pressure-sensitive adhesive composition of the present invention comprises an adhesive polymer A and an adhesive polymer B each having a specific monomer composition and a specific weight-average molecular weight, and further contains a liquid plasticizer.

The adhesive polymer A in the present invention is a polymer obtained by copolymerizing one or more alkyl (meth)acrylates with N-vinyl-2-pyrrolidone.

Examples of the alkyl (meth)acrylates include alkyl (meth)acrylates having a linear or branched alkyl group having from 4 to 12 carbon atoms as the ester side chain. When adhesion to the skin, low skin-irritating properties, and the like are taken into account, it is especially preferred that alkyl (meth)acrylates in which the side-chain ester group has from 4 to 9 carbon atoms, among those (meth)acrylates, be used alone or in combination of two or more thereof.

Preferred examples of such alkyl (meth)acrylates include butyl (meth)acrylate and 2-ethylhexyl (meth)acrylate.

In preparing the adhesive polymer A, one or more comonomers copolymerizable with the alkyl (meth)acrylates and with N-vinyl-2-pyrrolidone can be copolymerized with them, if desired.

Examples of such comonomers include monomers having one or more carboxyl groups, such as (meth)acrylic acid, itaconic acid, maleic acid, and maleic anhydride; monomers having a sulfo group, such as styrenesulfonic acid, allylsulfonic acid, sulfopropyl (meth)acrylate, (meth)acryloyloxynaphthalenesulfonic acid, and (meth)acrylamidomethylpropanesulfonic acid; monomers having a hydroxyl group, such as hydroxyethyl (meth)acrylate and hydroxypropyl (meth)acrylate; aminoalkyl (meth)acrylates such as aminoethyl (meth)acrylate, dimethylaminoethyl (meth)acrylate, and t-butylaminoethyl (meth)acrylate; alkoxyalkyl (meth)acrylates such as methoxyethyl (meth)acrylate, ethoxyethyl (meth)acrylate, and tetrahydrofurfuryl (meth)acrylate; alkoxyalkylene glycol esters of (meth)acrylic acid, such as the methoxyethylene glycol ester of (meth)acrylic acid, methoxydiethylene glycol ester of (meth)acrylic acid, methoxypolyethylene glycol ester of (meth)acrylic acid, and methoxypolypropylene glycol ester of (meth)acrylic acid; (meth)acrylonitrile; and compounds having a vinyl group, such as vinyl acetate and vinyl propionate. These comonomers may be copolymerized alone or in combination of two or more thereof.

The monomer composition of the adhesive polymer A should be suitably regulated according to the properties required of the medical non-crosslinked pressure-sensitive adhesive composition. However, one or more alkyl (meth)acrylates are polymerized in an amount of generally 50% by weight or larger, preferably from 50 to 90% by weight, and N-vinyl-2-pyrrolidone is copolymerized in an amount of preferably from 10 to 50% by weight based on the total weight of the monomers.

In the case where one or more comonomers copolymerizable with the alkyl (meth)acrylates and with N-vinyl-2-pyrrolidone are copolymerized as constituent monomers for the adhesive polymer A, the copolymerizable comonomers are used in place of part of the alkyl (meth)acrylates to be polymerized. It is, however, preferred that the alkyl (meth)acrylates be used in an amount of at least 50% by weight based on all monomers as stated above.

Consequently, the proportion of units derived from alkyl (meth)acrylates, that of units derived from N-vinyl-2-pyrrolidone, and that of units derived from comonomers copolymerizable with these are preferably regulated to from 50 to 90% by weight, from 10 to 50% by weight, and from 0 to 40% by weight, respectively, based on the adhesive polymer A.

When the proportion of units derived from alkyl (meth)acrylates is less than 50% by weight, there are cases where the medical non-crosslinked pressure-sensitive adhesive composition cannot exhibit a sufficient skin adhesive force. Consequently, the amount of the alkyl (meth)acrylates to be polymerized is preferably 50% by weight or larger, more preferably 65% by weight or larger.

With respect to the proportion of units derived from N-vinyl-2-pyrrolidone, proportions thereof less than 10% by weight may result in cases where the medical non-crosslinked pressure-sensitive adhesive composition may not have a sufficient cohesive force. On the other hand, in case where N-vinyl-2-pyrrolidone is copolymerized in an amount exceeding 50% by weight, there is the possibility that the adhesive polymer A might have a too high glass transition point and reduced tackiness.

In addition, too high proportions of N-vinyl-2-pyrrolidone units may result in impaired compatibility with the adhesive polymer B, which will be described later, and with liquid plasticizers. In this case, there is the possibility that when a liquid plasticizer is incorporated in a large amount, this liquid plasticizer may not be sufficiently held.

For those reasons, the proportion of N-vinyl-2-pyrrolidone units in the adhesive polymer A is preferably from 10 to 50% by weight. The proportion thereof is more preferably from 15 to 30% by weight when a balance between adhesion to the skin and cohesive force is taken into account. Furthermore, by regulating the proportion thereof to a value in the range of from 18 to 25% by weight, an excellent adhesive polymer A having a good balance between skin adhesive force and cohesive force is obtained.

Because the adhesive polymer A contains N-vinyl-2-pyrrolidone units, it shows a higher cohesive force than adhesive polymers containing no N-vinyl-2-pyrrolidone units. When this adhesive polymer A is used in combination with the adhesive polymer B according to the present invention, which will be described later, the two polymers produce a synergistic effect to heighten the cohesive force and tackiness of the adhesive polymers as a whole. The resulting blend hence can exhibit a sufficiently high cohesive force and skin adhesive force even when a liquid plasticizer is incorporated therein in a large amount.

The weight-average molecular weight of the adhesive polymer A according to the present invention is in the range of from 500,000 to 1,000,000, more preferably from 700,000 to 900,000. When the adhesive polymer A is regulated so as to have a weight-average molecular weight within that range, use of this polymer in combination with the adhesive polymer B, which will be described later, enables the resulting blend to exhibit a high cohesive force and a sufficient skin adhesive force, which are features of the medical non-crosslinked pressure-sensitive adhesive composition of the present present invention.

In the present invention, the weight-average molecular weight of an adhesive polymer prepared can be determined by dissolving the polymer in a solvent such as, e.g., tetrahydrofuran or dimethyl sulfoxide and subjecting the solution to gel permeation chromatography under the conditions shown in the Examples which will be given later.

The adhesive polymer B is either a polymer obtained by the polymerization of one or more alkyl (meth)acrylates or a polymer obtained by copolymerizing one or more alkyl (meth)acrylates with one or more comonomers other than N-vinyl-2-pyrrolidone.

The term "polymer obtained by polymerization" as used in the present invention means not only any polymer produced from one alkyl (meth)acrylate as the only constituent monomer but also any polymer obtained by copolymerizing two or more alkyl (meth)acrylates.

Namely, any polymer produced from one or more alkyl (meth)acrylates as the only constituent monomer(s) is usable as the "polymer obtained by polymerization" in the present invention regardless of the kinds and composition of the constituent monomers.

As the alkyl (meth)acrylates can be used the same alkyl (meth)acrylates enumerated above in the explanation of the adhesive polymer A. Those alkyl (meth)acrylates can be used alone or in combination of two or more thereof.

The alkyl (meth)acrylate(s) to be used for the adhesive polymer A may differ from the alkyl (meth)acrylate(s) to be used for the adhesive polymer B. It is, however, preferred to select the same alkyl (meth)acrylate(s) for the two adhesive polymers so as to attain satisfactory compatibility.

In the case where the two adhesive polymers each are produced from two or more alkyl (meth)acrylates as constituent monomers, it is preferred to use not only the same alkyl (meth)acrylates but also the same weight ratio between these alkyl (meth)acrylates.

Even when the adhesive polymer A and the adhesive polymer B differ from each other in the proportion between the constituent alkyl (meth)acrylates, the effect of the present invention is not lost. However, in the case where the two adhesive polymers are made to be equal to each other in the kinds of the alkyl (meth)acrylates and in the weight ratio between these (meth)acrylates therein, the two adhesive polymers are more compatible with each other.

In preparing the adhesive polymer B, one or more comonomers other than the alkyl (meth)acrylates can be copolymerized. As these comonomers can be used the comonomers enumerated above as examples in the explanation of the adhesive polymer A (provided that N-vinyl-2-pyrrolidone is excluded).

In the case where the adhesive polymer B is a copolymer of one or more alkyl (meth)acrylates and one or more of those comonomers, the proportion of units derived from the alkyl (meth)acrylate(s) in the adhesive polymer B is desirably regulated to at least 50% by weight, preferably to a value in the range of from 60 to 95% by weight, in order to balance adhesion to the skin, low skin-irritating properties, compatibility with the adhesive polymer A and liquid plasticizers, and other properties. This regulation brings about an improved balance among these properties. When the proportion of the units is regulated to 70 to 85% by weight, an adhesive polymer having a highly excellent balance among these properties is obtained.

In case where the proportion of alkyl (meth)acrylate units in the adhesive polymer B is less than 50% by weight, various properties of the adhesive polymer B are considerably influenced by the comonomer(s) copolymerized. This adhesive polymer B may have impaired compatibility with the adhesive polymer A and liquid plasticizers, resulting in cases where the medical non-crosslinked pressure-sensitive adhesive composition of the present invention may not be sufficiently exhibit its properties.

The weight-average molecular weight of the adhesive polymer B is in the range of from 1,000,000 to 1,500,000, more preferably from 1,100,000 to 1,300,000. In the present invention, the adhesive polymer B, which has a molecular weight within this range, is used in combination with the adhesive polymer A, whereby a medical non-crosslinked pressure-sensitive adhesive composition which exhibits a high cohesive force and a sufficient skin adhesive force is obtained.

In the pressure-sensitive adhesive composition of the present invention, the ratio of the proportion of the adhesive polymer A to that of the adhesive polymer B is preferably in the range of from 1:4 to 4:1 by weight from the standpoint of accomplishing the object of the present invention which is to exhibit both a skin adhesive force and low skin-irritating properties while attaining a good balance between these. When the two adhesive polymers are mixed in a ratio in the range of from 1:2 to 2:1, a further improved balance between the two properties is obtained. In particular, when the ratio is regulated so as to be in the range of from 1:1.5 to 1.5:1, a medical non-crosslinked pressure-sensitive adhesive composition which exhibits extremely satisfactory properties is obtained.

With respect to the proportions of the two adhesive polymers, when the proportion of the adhesive polymer A is too high, the non-crosslinked pressure-sensitive adhesive composition obtained by mixing the adhesive polymers A and B exhibits a high skin adhesive force due to the high skin adhesive force inherent in the adhesive polymer A. In this case, however, the ability of the adhesive polymer A itself to hold liquid plasticizers is not so high, so that mixing with such a small amount of the adhesive polymer B may not significantly improve the liquid-plasticizer-holding ability of the medical non-crosslinked pressure-sensitive adhesive composition obtained by the mixing of the adhesive polymers A and B.

Consequently, a liquid plasticizer cannot be incorporated in a sufficiently large amount into such a blend of the adhesive polymers A and B. There are cases where the resulting pressure-sensitive adhesive composition may be unsuitable for use in adhesive sheets for application to the skin, which are required to have moderately reduced skin-irritating properties.

On the contrary, in case where the proportion of the adhesive polymer B is too high, the pressure-sensitive adhesive composition obtained by mixing the adhesive polymers A and B may have reduced resistance to perspiration from the skin because of the poor sweat resistance of the adhesive polymer B. There is hence the possibility that the skin adhesive force of the pressure-sensitive adhesive layer might decrease.

As the liquid plasticizer to be used in the present invention, a plasticizer to be selected is liquid at room temperature and is compatible with the adhesive polymer A and the adhesive polymer B to enable the formation of a homogeneous pressure-sensitive adhesive layer. The incorporation of such a liquid plasticizer into the pressure-sensitive adhesive layer of the medical adhesive sheet of the present invention plasticizes the pressure-sensitive adhesive layer and enables the adhesive layer to give a soft wear feeling after application to the skin and to have reduced skin-irritating properties.

Examples of the liquid plasticizer include fatty acid esters formed from a monovalent saturated fatty acid having from 12 to 18 carbon atoms and a monohydric alcohol having from 1 to 8 carbon atoms, such as isopropyl myristate, isotridecyl myristate, ethyl laurate, ethyl oleate, and octyl palmitate; fatty acids having from 8 to 10 carbon atoms; glycols such as ethylene glycol, diethylene glycol, triethylene glycol, polyethylene glycol, propylene glycol, and polypropylene glycol; fats and oils such as olive oil, castor oil, squalene, and lanolin; organic solvents such as ethyl acetate, ethyl alcohol, dimethyl decyl sulfoxide, methyl octyl sulfoxide, dimethyl sulfoxide, dimethylformamide, dimethylacetamide, dimethyllauramide, dodecylpyrrolidone, and isosorbitol; liquid surfactants; known plasticizers such as diisopropyl adipate, phthalic esters, and diethyl sebacate; hydrocarbons such as liquid paraffins; and other compounds such as ethoxy stearyl alcohols, glycerol esters (which are liquid at room temperature), 1,3-propanediol, and glycerols. These may be used alone or in combination of two or more thereof.

Of the liquid plasticizers shown above, the fatty acid esters are preferred from the standpoints of compatibility with various adhesive polymers, moderate adhesion to the skin, low volatility in a heating step druing production, etc. It is preferred to use one or more esters obtained by reacting a monohydric alcohol having from 1 to 8 carbon atoms, such as methyl alcohol, ethyl alcohol, propyl alcohol, or isopropyl alcohol, as an alcohol ingredient with a monovalent saturated fatty acid having from 12 to 18 carbon atoms, such as myristic acid, palmitic acid, stearic acid, or oleic acid.

Especially preferred of those fatty acid esters are esters of a monohydric alcohol having from 1 to 5 carbon atoms with a monovalent saturated fatty acid having from 12 to 16 carbon atoms. Specifically, it is preferred to use isopropyl myristate, ethyl laurate, octyl palmitate, or the like.

The amount of the liquid plasticizer to be contained is generally from 10 to 240 parts by weight, preferably from 40 to 180 parts by weight, more preferably from 60 to 150 parts by weight, per 100 parts by weight of the sum of the adhesive polymer A and adhesive polymer B.

One or more adhesive polymers other than the adhesive polymer A and adhesive polymer B may be added as an optional ingredient to the medical non-crosslinked pressure-sensitive adhesive composition of the present invention for the purpose of regulating pressure-sensitive adhesive properties as will be described later. In this case, that amount of the liquid plasticizer to be contained is based on the sum of the adhesive polymer A, the adhesive polymer B, and the adhesive polymers having a constitution different from those of the adhesive polymers A and B.

In case where the amount of the liquid plasticizer contained is smaller than 10 parts by weight per 100 parts by weight of the sum of the adhesive polymers, the pressure-sensitive adhesive layer may be in an insufficiently plasticized state and, hence, the reduction in skin adhesive force may be insufficient. As a result, there are cases where skin-irritating properties may not be sufficiently reduced.

On the contrary, when a liquid plasticizer is incorporated in an amount exceeding 240 parts by weight per 100 parts by weight of the adhesive polymers, there are cases where the liquid plasticizer cannot be held in the pressure-sensitive adhesive layer while attaining a sufficient cohesive force. As a result, there are cases where the liquid plasticizer blooms on the surface of the pressure-sensitive adhesive layer to excessively reduce the skin adhesive force.

Ingredients other than those explained above can be suitably incorporated into the medical non-crosslinked pressure-sensitive adhesive composition of the present invention in order to improve the pressure-sensitive adhesive properties and stability of the adhesive. Examples thereof include adhesive polymers having a constitution different from those of the adhesive polymers A and B, solid plasticizers, stabilizers including antioxidants, and extenders.

In case where such ingredients are incorporated in a large amount, the proportion of all adhesive polymers in the medical non-crosslinked pressure-sensitive adhesive composition to the other ingredients may be reduced. As a result, there may be cases where an adverse influence is exerted on the effect of the medical non-crosslinked pressure-sensitive adhesive composition of the present invention that a liquid plasticizer can be contained in a large amount. Consequently, those optional ingredients each is added in a minimum amount necessary for producing its effect or in an amount slightly larger than that.

The proportion of those optical ingredients is, for example, in the range of from 1 to 20 parts by weight, preferably from 1 to 10 parts by weight, more preferably from 1 to 5 parts by weight, per 100 parts by weight of the sum of all adhesive polymers. The smaller the proportion thereof, the more the adverse influence on the properties of the pressure-sensitive adhesive layer can be reduced.

Besides the ingredients shown above, a percutaneously absorbable drug may be incorporated into the medical non-crosslinked pressure-sensitive adhesive layer. For example, a corticosteroid, analgesic anti-inflammatory agent, hypnotic sedative, tranquilizer, antihypertensive, hypotensive diuretic, antibiotic, anesthetic, antibacterial, antifungal, vitamin, coronary vasodilator, antihistaminic, cough medicine, sex hormone, antidepressant, cerebral vasodilator, antinauseant, antitumor agent, biomedicine, or the like can be suitably selected and incorporated according to the intended medical treatment.

It is preferred to use a hydrophobic drug among those drugs from the standpoints of dispersibility in the pressure-sensitive adhesive composition and percutaneous absorbability. The term "hydrophobic" as used herein means that the drug has a solubility of 0.4 g or lower in 100 g of 25° C. distilled water.

The proportion of such a drug in the pressure-sensitive adhesive composition is suitably determined according to the kind of the drug and the intended medical treatment. It is, however, preferred that the proportion thereof in the medical non-crosslinked pressure-sensitive adhesive layer should be from 0.1 to 60% by weight, preferably from 1 to 40% by weight, more preferably from 3 to 30% by weight.

When the proportion of the drug contained is lower than 0.1% by weight, there are cases where the drug may not be expected to be percutaneously administered in an amount effective in the medical treatment, although this depends on the kind of the drug. On the other hand, even when a drug is incorporated in a proportion exceeding 60% by weight, the therapeutic effect thereof is not always enhanced to a level which compensates for such a high content. Such high proportions may hence be uneconomical. In addition, there are cases where the incorporation of too large an amount of a drug reduces the cohesive force of the pressure-sensitive adhesive composition and this exerts an adverse influence on properties of the medical non-crosslinked pressure-sensitive adhesive composition, such as, e.g., adhesion to the skin.

A preferred process for producing the medical non-crosslinked pressure-sensitive adhesive composition of the present invention will be explained below.

For producing the medical non-crosslinked pressure-sensitive adhesive composition of the present invention, it is necessary to separately prepare an adhesive polymer A and an adhesive polymer B in advance. For example, the process described below can be used to prepare adhesive polymers having preferred properties as the adhesive polymer A and adhesive polymer B according to the present invention. By mixing these polymers by the procedure shown below, a medical non-crosslinked pressure-sensitive adhesive composition of the present invention can be produced.

In preparing an adhesive polymer A for use in the medical non-crosslinked pressure-sensitive adhesive composition of the present invention, one or more alkyl (meth)acrylates are copolymerized with N-vinyl-2-pyrrolidone and optionally with one or more comonomers other than N-vinyl-2-pyrrolidone which are copolymerizable with them. This copolymerization is preferably conducted by solution polymerization in a hydrophobic solvent to prepare an adhesive polymer having a weight-average molecular weight of from 500,000 to 1,000,000.

As the hydrophobic solvent in this reaction may be used ethyl acetate, toluene, hexane, or the like.

On the other hand, in preparing an adhesive polymer B, it is preferred that one or more starting-material monomers comprising one or more alkyl (meth)acrylates and optionally including one or more comonomers other than N-vinyl-2-pyrrolidone should be polymerized by the emulsion polymerization method to prepare an adhesive polymer having a weight-average molecular weight of from 1,000,000 to 1,500,000.

Although these adhesive polymers A and B and a liquid plasticizer are mixed together in preparing the medical non-crosslinked pressure-sensitive adhesive composition of the present invention, these three ingredients are extremely difficult to be mixed by a mere mixing operation. This is because the liquid containing the adhesive polymer A prepared above and the liquid plasticizer are hydrophobic, while the liquid containing the adhesive polymer B prepared above is an aqueous emulsion. Consequently, the process of the present invention for producing the medical non-crosslinked pressure-sensitive adhesive composition is characterized in that those ingredients are mixed through the following steps.

In the present invention, a liquid plasticizer is gradually incorporated, with stirring, into the liquid containing the adhesive polymer B to thereby swell the adhesive polymer B. In this operation, when a liquid plasticizer alone is incorporated, there occasionally are cases where the swelling of the adhesive polymer B is less apt to proceed. For avoiding this problem, it is preferred to incorporate a lower alcohol either beforehand or simultaneously with the liquid plasticizer, according to need. As a result, the adhesive polymer B is swollen more rapidly.

The lower alcohol to be incorporated here functions as a swelling aid. Not a lower amide, a surfactant, or the like but a lower alcohol is selectively used. This is because lower alcohols are highly effective in helping the swelling of the adhesive polymer B, and because these alcohols have a low boiling point and can hence be easily removed in, e.g., a drying step in the production of an adhesive sheet or the like.

As the lower alcohol may be used a monohydric alcohol having from 1 to 4 carbon atoms. Examples thereof include methanol, ethanol, isopropanol, and n-butanol.

The amount of the lower alcohol to be incorporated may be suitably regulated according to the mixed state of the adhesive polymer B and liquid plasticizer. However, the amount thereof is generally from $1/15$ to $1/2$, preferably from $1/15$ to $1/3$, the amount of the liquid plasticizer incorporated.

In case where the amount of the lower alcohol incorporated is too small, the effect of helping the swelling of the adhesive polymer B with the liquid plasticizer may be insufficient. On the other hand, in case where the amount of the alcohol incorporated is too large, the emulsion suffers phase separation and the adhesive polymer B may aggregate and separate out from the liquid. There are cases where even when this adhesive polymer B is mixed with the liquid containing the adhesive polymer A in a later step, it is difficult to evenly mix these.

After the adhesive polymer B is swollen in the step described above, it is mixed with the liquid containing the adhesive polymer A which has been separately prepared beforehand. The resulting mixture is homogenized to thereby prepare a liquid containing the medical non-crosslinked pressure-sensitive adhesive composition of the present invention. For this mixing, use may be made of either a method in which the adhesive polymer B is added to and mixed with the liquid containing the adhesive polymer A or the reverse method, i.e., a method in which the adhesive polymer A is added to and mixed with the liquid containing the adhesive polymer B.

In the mixing of the liquid containing the adhesive polymer A with the liquid containing the adhesive polymer B, a hydrophobic solvent may be added simultaneously with the liquid containing the adhesive polymer A or the liquid containing the adhesive polymer B. This addition of a hydrophobic solvent further facilitates the production of the medical non-crosslinked pressure-sensitive adhesive composition of the present invention.

By incorporating a hydrophobic solvent into the liquid containing the adhesive polymer A and/or the liquid containing the adhesive polymer B before mixing the two liquids, the viscosity of the liquid containing the adhesive polymer A and/or the liquid containing the adhesive polymer B is reduced moderately and the efficiency of stirring is improved to enhance compatibility. In addition, the adhesive polymer B in the liquid containing the same is more swollen with the hydrophobic solvent and this liquid is hence more compatible with that liquid containing the adhesive polymer A which is a hydrophobic solution.

The hydrophobic solvent to be used here preferably is the same as the hydrophobic solvent used in preparing the adhesive polymer A. Use of this solvent makes the liquid containing the adhesive polymer B and the liquid containing the adhesive polymer A more alike in composition during mixing, whereby the compatibility of the two liquids is further improved. Although the amount of the hydrophobic solvent to be used in mixing the liquid containing the adhesive polymer A with the liquid containing the adhesive polymer B may be suitably selected, the solvent should not be incorporated in a too large amount.

One of the reasons for this is as follows. In case where a large amount of a hydrophobic solvent is incorporated into the liquid containing the adhesive polymer B, the adhesive polymer B swells excessively. As a result, there are cases where the emulsion state of the liquid containing the adhesive polymer B is destroyed to cause phase inversion and this liquid hence has impaired compatibility with the liquid containing the adhesive polymer A.

On the other hand, the liquid containing the adhesive polymer A, which has been prepared through solution polymerization in a hydrophobic solvent, is free from that problem. However, the hydrophobic solvent should not be added in too large an amount because the hydrophobic solvent is an ingredient to be removed in producing an adhesive sheet and the incorporation of the solvent in a large amount is wastes of resources and of energy for removal.

In the case where ingredients such as, e.g., additives, a percutaneously absorbable drug, and an adhesive polymer other than the adhesive polymers A and B are further incorporated into the medical non-crosslinked pressure-sensitive adhesive composition of the present invention thus produced, it is preferred that such ingredients should be added after the liquid containing the adhesive polymer A and the liquid containing the adhesive polymer B have been mixed with each other in the step described above.

The liquid containing the adhesive polymer A and the liquid containing the adhesive polymer B are difficult to be mixed with each other as described above. In order to overcome this problem, the mixing operation in the process of the present invention for producing a medical non-crosslinked pressure-sensitive adhesive composition is conducted by the procedure described above.

In the case where additives, another adhesive polymer, and the like are added in the mixing step, there is the possibility that the liquid containing the adhesive polymer A and the liquid containing the adhesive polymer B cannot be satisfactorily mixed with each other even by the procedure described above. It is therefore preferred to add those ingredients after the mixing of the two adhesive polymers has been completed to prepare the medical non-crosslinked pressure-sensitive adhesive composition of the present invention.

However, it is a matter of course that as long as the liquid containing the adhesive polymer A and the liquid containing the adhesive polymer B have been ascertained, through a preliminary test or the like, to be easily mixable, additives and an adhesive polymer other than the adhesive polymers A and B can be satisfactorily added during the step of mixing the liquid containing the adhesive polymer A with the liquid containing the adhesive polymer B.

The liquid thus prepared, which contains the medical non-crosslinked pressure-sensitive adhesive composition of the present invention, can be used as a pressure-sensitive adhesive solution for producing a medical adhesive sheet. The intended use of the adhesive sheet, the feeling to be given by the adhesive sheet during wear, handling in application and removal, etc. are taken into account when the constitution of the adhesive sheet is determined. Preferred constitutions of the medical adhesive sheets employing the medical non-crosslinked pressure-sensitive adhesive composition of the present invention will be explained below.

Any support may be used as long as it is impermeable to the adhesive polymers and liquid plasticizer contained in the pressure-sensitive adhesive layer. For example, use may be made of a resin film or sheet made of a polyester, polyamide, poly(vinyl chloride), polyethylene, polypropylene, ethylene/vinyl acetate copolymer, polytetrafluoroethylene, or ionomer resin, a metal foil, or the like. A multilayered support comprising two or more superposed layers selected from such films, sheets, and foils may also be used.

In case where such a film, sheet, etc. which is too thick is used as the support, the medical adhesive sheet not only gives a poor wear feeling but also has reduced moisture permeability, resulting in the possibility that water transpiration from the skin might be inhibited. These properties are hence taken into account in selecting the material, thickness, etc. of the support.

It is also possible to use a multilayered support comprising a nonporous support, e.g., a resin film or a metal foil, and a porous support, e.g., a fabric such as a nonwoven fabric or woven fabric, paper, or a perforated resin sheet. Use of this multilayered support is preferred because when a pressure-sensitive adhesive layer is formed on the porous-support side, the pressure-sensitive adhesive layer moderately penetrates into pores of the porous support to thereby produce an effect that anchoring between the pressure-sensitive adhesive layer and the multilayered support is improved.

In case where a nonporous support which is too thick is used, the medical adhesive sheet not only may give an impaired wear feeling but also may have reduced moisture permeability, resulting in the possibility that water transpiration from the skin might be inhibited. Consequently, it is preferable to avoid use of a too thick support.

The thickness of the support is preferably selected in the range of from 10 to 500 μm although it depends on the material constituting the support. The thickness thereof is especially preferably from 10 to 100 μm. In the case where a porous support is used, the basis weight thereof is preferably from 5 to 30 g/m². By using a support having a thickness or basis weight within that range, the adhesive sheet can exhibit satisfactory properties without causing a decrease in wear feeling.

A support having a thickness and a basis weight which have been regulated so as to be within those ranges has flexibility and moderate toughness. As a result, the adhesive sheet has satisfactory handleability in application and stripping, while the influences of the support on the wear feeling and water transpiration from the skin are reduced. Furthermore, use of such support produces an effect that the pressure-sensitive adhesive layer moderately penetrates into the support to improve the anchoring of the pressure-sensitive adhesive layer to the support.

The thickness of the pressure-sensitive adhesive layer, which is formed on at least one side of the support, may be determined while taking account of adhesion to the skin and skin-irritating properties and, in the case of incorporating a percutaneously absorbable drug into the pressure-sensitive adhesive layer, the necessary amount, percentage utilization, etc. of the drug. However, the thickness thereof is generally from 10 to 200 μm, preferably from 30 to 100 μm.

When the thickness of the pressure-sensitive adhesive layer is smaller than 10 μm, there are cases where sufficient adhesion to the skin may not be exhibited and the adhesive sheet may peel off during wear. On the other hand, in case where the thickness thereof exceeds 200 μm, the adhesive sheet itself may have heightened rigidity and may give an enhanced uncomfortable feeling during wear. As long as the thickness of the pressure-sensitive adhesive layer is regulated so as to be within that range, the adhesive sheet shows sufficient adhesion to the skin and is less apt to pose a problem concerning skin-irritating properties or wear feeling.

It is, however, a matter of course that the pressure-sensitive adhesive layer may have a thickness exceeding the upper limit when there is a special reason, e.g., in the case where a percutaneously absorbable drug is incorporated in an extremely large amount into the pressure-sensitive adhesive layer.

The medical adhesive sheet of the present invention is regulated so that-the thickness thereof, i.e., the distance between the surface of the pressure-sensitive adhesive layer and the surface of the support, is in the range of preferably from 20 to 700 μm, more preferably from 20 to 300 μm, even more preferably from 20 to 100 μm. This is because too large thicknesses may result in an impaired wear feeling and too small thicknesses may result in reduced handleability in application and stripping.

The medical adhesive sheet of the present invention can be produced, for example, by the following processes.

A first process comprises applying the liquid prepared above which contains the medical non-crosslinked pressure-sensitive adhesive composition to a support and then drying the coating to remove the water and other ingredients including the hydrophobic solvent and lower alcohol and thereby form a pressure-sensitive adhesive layer. For the purpose of protecting the pressure-sensitive adhesive layer of the medical adhesive sheet thus produced, a separator which can be easily stripped off is usually superposed on the pressure-sensitive adhesive layer.

A second process comprises applying the liquid containing the medical non-crosslinked pressure-sensitive adhesive composition to a separator on its side which has undergone a releasability-imparting treatment, drying the coating to remove the water and other ingredients including the hydrophobic solvent and lower alcohol and thereby form a pressure-sensitive adhesive layer, and transferring this pressure-sensitive adhesive layer to one side of a support.

The present invention will be explained below in detail by reference to Examples of the present invention and Comparative Examples. In the following description, "parts" means "parts by weight" and "%" means "% by weight", unless otherwise indicated.

Adhesive polymers for use in producing pressure-sensitive adhesive compositions of the Examples and Comparative Examples were prepared in the following manners. Adhesive polymers A1 and A2 correspond to the adhesive polymer A in the present invention, while adhesive polymers B1, B2, and C1 correspond to the adhesive polymer B in the present invention. Adhesive polymer C2 corresponds to neither the adhesive polymer A in the present invention nor the adhesive polymer B in the present invention.

Preparation of Adhesive Polymers A1 and A2

Ethyl acetate was used as the hydrophobic solvent shown in Table 1. Thereto were added the monomers and polymerization initiator shown in Table 1. A polymerization reaction was conducted at 60° C. in an inert gas atmosphere. Thus, adhesive polymers A1 and A2 were prepared.

Preparation of Adhesive Polymers B1 and B2

Water, an emulsifying agent, and the monomers shown in Table 1 were subjected to emulsion polymerization. The monomers were dispersed in the water to obtain an emulsion. In an inert gas atmosphere, the polymerization initiator was added to conduct a polymerization reaction at 70° C. Thus, adhesive polymers B1 and B2 were prepared.

Preparation of Adhesive Polymers C1 and C2

A polymerization reaction was conducted in the same manner as in "Preparation of Adhesive Polymers A1 and A2", except that the monomers and the polymerization initiator were changed as shown in Table 1. Thus, adhesive polymers C1 and C2 were prepared.

After the preparation of the adhesive polymers, the weight-average molecular weight of each adhesive polymer was measured by gel permeation chromatography under the following analysis conditions. The results obtained are shown in Table 1.

Analysis Conditions

GPC apparatus: HLC8120 (manufactured by Tosoh Corp.)
Column: TSKgelGM$_{HHR-H}$+TSKgelGM$_{HHR-H}$+TSKgel2000H$_{HR}$ (each manufactured by Tosoh Corp.)
Eluent: tetrahydrofuran
Flow rate: 1.0 mL/min
Measuring temperature: 40° C.
Detector: differential refractometer

TABLE 1

| | | Amount incorporated [parts] | | | | | |
|---|---|---|---|---|---|---|---|
| | | A1 | A2 | B1 | B2 | C1 | C2 |
| Monomer | 2EHA | 75 | 75 | 77 | 75 | 95 | 60 |
| | NVP | 22 | 25 | — | — | — | — |
| | AA | 3 | — | — | 5 | 5 | — |
| | MA | — | — | 23 | — | — | — |
| | IBA | — | — | — | 20 | — | — |
| | MEA | — | — | — | — | — | 30 |
| | HEMA | — | — | — | — | — | 10 |
| Polymerization initiator | BPO | — | 0.2 | — | — | 0.2 | — |
| | AIBN | 0.2 | — | — | — | — | 0.2 |
| | PO2SA | — | — | 0.3 | 0.4 | — | — |
| Polymerization method | | solution polymerization | solution polymerization | emulsion polymerization | emulsion polymerization | solution polymerization | solution polymerization |
| Weight-average molecular weight [×10000] | | 70 | 90 | 120 | 115 | 150 | 60 |

2EHA: 2-ethylhexyl acrylate
NVP: N-vinyl-2-pyrrolidone
AA: acrylic acid
MA: methyl acrylate
IBA: isobutyl acrylate
MEA: 2-methoxyethyl acrylate
HEMA: 2-hydroxyethyl methacrylate
BPO: benzoyl peroxide
AIBN: azobisisobutyronitrile
PO2SA: ammonium persulfate The adhesive polymers prepared were used according to the formulations shown in Table 2 to prepare pressure-sensitive adhesive compositions of the Examples and Comparative Examples in the following manners. These pressure-sensitive adhesive compositions were used to produce medical adhesive sheets.

EXAMPLE 1

Isopropyl myristate was gradually mixed as a liquid plasticizer with the liquid containing adhesive polymer B1, which had been prepared by the emulsion polymerization method, to swell the adhesive polymer B1. In the mixing, methanol was added (in an amount 1/12 the amount of the isopropyl myristate) together with the isopropyl myristate in order to more rapidly swell the adhesive polymer.

After the swelling of adhesive polymer B1, the liquid containing adhesive polymer A1, which had been prepared by the solution polymerization method, was gradually mixed with the liquid containing adhesive polymer B1. Thus, a medical non-crosslinked pressure-sensitive adhesive composition was prepared.

In this mixing, ethyl acetate was added together with the liquid containing adhesive polymer A1 in order to more rapidly mix the liquid containing adhesive polymer B1 with the liquid containing adhesive polymer A1.

The liquid thus prepared, which contained the medical non-crosslinked pressure-sensitive adhesive composition, was applied to the releasability-imparted side of a separator made of a polyester, in such an amount as to result in a pressure-sensitive adhesive layer thickness after drying of 50 μm. The coating was dried at 100° C. for 5 minutes to form a pressure-sensitive adhesive layer. Thereafter, this pressure-sensitive adhesive layer was transferred to the nonwoven-fabric side of a multilayered support comprising a nonwoven polyester fabric (basis weight, 8 g/m²) and a polyester film (thickness, 2 μm). Thus, a medical adhesive sheet was produced.

EXAMPLES 2 TO 4

A medical adhesive sheet was produced in the same manner as in Example 1, except that the proportions of the adhesive polymer and isopropyl myristate in Example 1 were changed as shown in Table 2.

EXAMPLE 5

The same procedure as in Example 1 was conducted, except that gallopamil hydrochloride, which is a percutaneously absorbable drug, was incorporated into the liquid containing the medical non-crosslinked pressure-sensitive adhesive composition before the liquid containing the medical non-crosslinked pressure-sensitive adhesive composition was applied to the releasability-imparted side of the separator made of a polyester. Thus, a medical adhesive sheet having a pressure-sensitive adhesive layer containing the percutaneously absorbable drug was produced.

COMPARATIVE EXAMPLE 1

A medical adhesive sheet was produced in the same manner as in Example 1, except that adhesive polymer C1 was used in place of the adhesive polymer A1 in Example 1.

COMPARATIVE EXAMPLE 2

The liquid containing adhesive polymer A1 was mixed with isopropyl myristate. An isocyanate crosslinking agent (Coronate HL; manufactured by Nippon Polyurethane Co., Ltd.) was further added thereto to prepare a medical crosslinked pressure-sensitive adhesive composition. This medical crosslinked pressure-sensitive adhesive composition was used to produce a medical adhesive sheet in the same manner as in Example 1.

COMPARATIVE EXAMPLES 3 AND 4

Isopropyl myristate was gradually added to the liquid containing adhesive polymer B1 or the liquid containing adhesive polymer B2 to swell the adhesive polymer. Thus, medical non-crosslinked pressure-sensitive adhesive compositions were prepared. These medical non-crosslinked pressure-sensitive adhesive compositions were used to produce medical adhesive sheets in the same manner as in Example 1.

COMPARATIVE EXAMPLE 5

Isopropyl myristate was gradually added to the liquid containing adhesive polymer B2 to swell the adhesive polymer B2. Thereafter, an isocyanate crosslinking agent (Coronate HL) was added thereto to prepare a medical crosslinked pressure-sensitive adhesive composition. This medical crosslinked pressure-sensitive adhesive composition was used to produce a medical adhesive sheet in the same manner as in Example 1.

COMPARATIVE EXAMPLE 6

The liquid containing adhesive polymer A1, the liquid containing adhesive polymer C2, and isopropyl myristate were mixed together to prepare a liquid containing a medical non-crosslinked pressure-sensitive adhesive composition. This pressure-sensitive adhesive composition was used to produce a medical adhesive sheet in the same manner as in Example 1.

COMPARATIVE EXAMPLE 7

The liquid containing adhesive polymer C1, the liquid containing adhesive polymer C2, and isopropyl myristate were mixed together to prepare a liquid containing a medical non-crosslinked pressure-sensitive adhesive composition. This pressure-sensitive adhesive composition was used to produce a medical adhesive sheet in the same manner as in Example 1.

COMPARATIVE EXAMPLE 8

A medical adhesive sheet having a pressure-sensitive adhesive layer containing a percutaneously absorbable drug was produced in the same manner as in Example 5, except that adhesive polymer C2 was used in place of the adhesive polymer A1 in Example 5.

COMPARATIVE EXAMPLE 9

The liquid containing adhesive polymer A1, the liquid containing adhesive polymer C2, and isopropyl myristate were mixed together to prepare a medical non-crosslinked pressure-sensitive adhesive composition. Gallopamil hydrochloride was incorporated into the resulting adhesive-containing liquid. Thus, a medical non-crosslinked pressure-sensitive adhesive composition containing the percutaneously absorbable drug was prepared. This pressure-sensitive adhesive composition was used to produce a medical adhesive sheet having a pressure-sensitive adhesive layer containing the percutaneously absorbable drug, in the same manner as in Example 5.

The medical adhesive sheets produced were subjected to a cohesive force test, skin adhesive force test, and skin irritation test. The results obtained are summarized in Table 2.
Cohesive Force Test The medical adhesive sheets of Examples 1 to 5 and Comparative Examples 1 to 9 each were cut into a square having an area of 10 cm². The separator was stripped from each adhesive sheet, and the pressure-sensitive adhesive layer was evaluated in the following three grades.

3: The pressure-sensitive adhesive layer has sufficient cohesive force and has not undergone migration of the liquid plasticizer to the pressure-sensitive adhesive layer surface, showing that compatibility is satisfactory.

2: The pressure-sensitive adhesive layer has sufficient cohesive force but has undergone migration of the liquid plasticizer to the pressure-sensitive adhesive layer surface, showing that compatibility is poor.

1: The pressure-sensitive adhesive layer has undergone cohesive failure.

The following was found from the results of the cohesive force test. In each of the adhesive sheets of Examples 1 to 5, which employed a medical non-crosslinked pressure-sensitive adhesive composition according to the present invention, the pressure-sensitive adhesive layer did not suffer cohesive failure upon separator stripping and showed an extremely high cohesive force. Furthermore, migration of the liquid plasticizer to the pressure-sensitive adhesive layer surface was not observed at all in each of these Examples.

In contrast, in each of the adhesive sheets of Comparative Examples 3 and 4, which employed one adhesive polymer as the only adhesive polymer constituting the pressure-sensitive adhesive layer, the pressure-sensitive adhesive layer suffered cohesive failure upon separator stripping. The cohesive force of the pressure-sensitive adhesive layers was clearly insufficient for these adhesive sheets to be used as medical adhesive sheets.

It was further found that even in the case where two adhesive polymers were used in combination, a high cohesive force such as that of the medical non-crosslinked pressure-sensitive adhesive compositions of the present invention was not obtained according to the combination as shown below. Such pressure-sensitive adhesive compositions were unusable for medical adhesive sheets.

First, in the medical adhesive sheets of Comparative Examples 1 and 7, which each employed two adhesive polymers each containing no N-vinylpyrrolidone units, the pressure-sensitive adhesive layer suffered cohesive failure in the cohesive force test.

Furthermore, also in the medical adhesive sheet of Comparative Example 6, in which adhesive polymer A1, which contained N-vinylpyrrolidone units, was employed as one of the two adhesive polymers, the pressure-sensitive adhesive layer suffered cohesive failure in the cohesive force test.

In this Comparative Example, adhesive polymer A1 was used in combination with adhesive polymer C2, which had a weight-average molecular weight of 600,000. This value of molecular weight is considerably smaller than the weight-average molecular weight of the adhesive polymer B for use in the present invention, which is in the range of from 1,000,000 to 1,500,000. It is thought that because of the low molecular weight of adhesive polymer C2, the pressure-sensitive adhesive composition prepared by mixing those two adhesive polymers was unable to exhibit the desired cohesive force.

The medical adhesive sheets of Comparative Examples 2 and 5 as other Comparative Examples, in which a crosslinked pressure-sensitive adhesive composition was used in place of a medical non-crosslinked pressure-sensitive adhesive composition to form a pressure-sensitive adhesive layer, were also subjected to the cohesive force test. As a result, the adhesive sheet of Comparative Example 2 underwent migration of the liquid plasticizer to the pressure-sensitive adhesive layer surface, while the adhesive sheet of Comparative Example 5 suffered the cohesive failure of the pressure-sensitive adhesive layer. In either case, a high cohesive force such as that attained with the medical non-crosslinked pressure-sensitive adhesive compositions of the present invention was not obtained.

These results showed that the pressure-sensitive adhesive compositions of the present invention have an extremely high cohesive force.

The same tendency was observed in the cohesive force test of the medical adhesive sheets having a pressure-sensitive adhesive layer containing a percutaneously absorbable drug. Specifically, in the medical adhesive sheet of Example 5, which is an embodiment of the present invention, migration of the liquid plasticizer to the pressure-sensitive adhesive layer surface was not observed after separator stripping and the liquid plasticizer was sufficiently held in the pressure-sensitive adhesive layer. In contrast, in the medical adhesive sheet of Comparative Example 8, in which a combination with an adhesive polymer containing no N-vinylpyrrolidone units was used to form the pressure-sensitive adhesive layer, migration of the liquid plasticizer to the pressure-sensitive adhesive layer surface was observed.

Furthermore, in the medical adhesive sheet of Comparative Example 9, in which an adhesive polymer containing N-vinylpyrrolidone units was used as one of the two adhesive polymers but the adhesive polymer used in combination therewith was an adhesive polymer having a weight-average molecular weight of 600,000, the pressure-sensitive adhesive layer suffered cohesive failure and was unable to exhibit a satisfactory cohesive force.

Skin Adhesive Force Test

The medical adhesive sheets (10 cm$^2$) of Examples 1 to 4 and Comparative Examples 1 to 7 were applied to inner parts of the upper arms of five volunteers. After the lapse of 24 hours, adhesion to the skin was visually evaluated. The adhesion to the skin of each medical adhesive sheet was evaluated in the following five grades, and the average for the five persons was taken as skin adhesive force.

5: The medical adhesive sheet was wholly adherent to the skin.
4: The medical adhesive sheet had peeled off in an area less than about 20%.
3: The medical adhesive sheet had peeled off in an area of about 20 to 40%.
2: The medical adhesive sheet had peeled off in an area of about 40 to 60%.
1: The medical adhesive sheet had peeled off in an area of about 60% or larger, or the pressure-sensitive adhesive layer had suffered cohesive failure.

The medical adhesive sheets of Examples 1 to 4, which each had a pressure-sensitive adhesive layer formed from a medical non-crosslinked pressure-sensitive adhesive composition of the present invention, each were sufficiently adherent to the skin until stripping. Any abnormality, e.g., migration, was not observed on the pressure-sensitive adhesive layer in stripping.

In contrast, the medical adhesive sheets of Comparative Example 1 and Comparative Examples 3 to 7 each suffered the cohesive failure of the pressure-sensitive adhesive layer upon stripping. More than one medical adhesive sheet showed adhesive remaining on the skin surface after stripping. These adhesive sheets were insufficient in the cohesive force of the pressure-sensitive adhesive layers.

In Comparative Example 2, cohesive failure did not occur unlike the other Comparative Examples because this adhesive sheet employed a crosslinked adhesive polymer. However, this adhesive sheet finally peeled off and failed to show a satisfactory skin adhesive force unlike the adhesive sheets employing medical non-crosslinked pressure-sensitive adhesive compositions of the present invention.

Skin Irritation Test

In the skin adhesive force test, the degree of pain caused by the stripping of each medical adhesive sheet applied was evaluated based on the following criteria. The average of the evaluations by the five persons was taken as skin-irritating properties.

5: No pain.
4: Slight pain was felt.
3: Pain was felt.
2: Somewhat intense pain was felt.
1: Considerably painful.

The medical adhesive sheets of Examples 1 to 4 each gave almost no pain upon stripping. The reason for this may be that the pressure-sensitive adhesive layer of each medical adhesive sheet contained a large amount of a liquid plasticizer and this enabled the adhesive layer to retain moderately reduced tackiness to the skin.

The results in the Comparative Examples are as follows. The medical adhesive sheet of Comparative Example 2, which employed a crosslinked pressure-sensitive adhesive composition, had low skin-irritating properties and could be stripped off satisfactorily. However, with respect to the remaining Comparative Examples, i.e., Comparative Examples 1 and 3 to 7, more than one adhesive sheet suffered the cohesive failure of the pressure-sensitive adhesive layer and was unable to be evaluated for skin-irritating properties.

In addition, since those medical adhesive sheets which suffered cohesive failure left a pressure-sensitive adhesive composition residue on the skin after stripping, it was necessary to completely remove the adhesive residue from the skin surface after the test. The pressure-sensitive adhesive compositions which cause such adhesive remaining are not practically usable in medical adhesive sheets.

TABLE 2

|  | Amount incorporated [(parts)] | | | | | Cohesive force test | Skin adhesive force test | skin irritation test |
|---|---|---|---|---|---|---|---|---|
|  | Adhesive polymer | | | Liquid plasticizer*[1] | Other ingredient*[2] | | | |
|  | A | B | C | | | | | |
| Ex. 1 | A1 (16) | B1 (24) | — | IPM (60) | — | 3 | 4.7 | 5.0 |
| Ex. 2 | A1 (16) | B2 (24) | — | IPM (60) | — | 3 | 3.8 | 4.4 |
| Ex. 3 | A1 (12) | B1 (18) | — | IPM (70) | — | 3 | 4.6 | 5.0 |
| Ex. 4 | A2 (16) | B1 (24) | — | IPM (60) | — | 3 | 3.9 | 4.4 |
| Ex. 5 | A1 (14) | B1 (21) | — | IPM (60) | drug (5) | 3 | NA*[3] | NA*[3] |
| Comp. Ex. 1 | — | B1 (24) | C1 (16) | IPM (60) | — | 1 | 1.6 | ND*[4] |
| Comp. Ex. 2 | A1 (40) | — | — | IPM (60) | crosslinking agent (0.12) | 2 | 1.8 | 4.2 |

TABLE 2-continued

| | Amount incorporated [(parts)] | | | | | Cohesive | Skin adhesive | skin |
|---|---|---|---|---|---|---|---|---|
| | Adhesive polymer | | | Liquid | Other | force | force | irritation |
| | A | B | C | plasticizer*1 | ingredient*2 | test | test | test |
| Comp. Ex. 3 | — | B1 (40) | — | IPM (60) | — | 1 | 1.2 | ND*4 |
| Comp. Ex. 4 | — | B2 (40) | — | IPM (60) | — | 1 | 1.2 | ND*4 |
| Comp. Ex. 5 | — | B2 (40) | — | IPM (60) | crosslinking agent (0.3) | 1 | 1.2 | ND*4 |
| Comp. Ex. 6 | A1 (20) | — | C2 (20) | IPM (60) | — | 1 | 1.3 | ND*4 |
| Comp. Ex. 7 | — | — | C1 (20) C2 (20) | IPM (60) | — | 1 | 1.0 | ND*4 |
| Comp. Ex. 8 | — | B1 (21) | C2 (14) | IPM (60) | drug (5) | 2 | NA | NA |
| Comp. Ex. 9 | A1 (17.5) | — | C2 (17.5) | IPM (60) | drug (5) | 1 | NA | NA |

(Note)
*1IPM (isopropyl myristate)
*2drug (gallopamil hydrochloride); crosslinking agent (Coronate HL)
*3NA: not conducted. (because drug was contained)
*4The pressure-sensitive adhesive layer was not satisfactorily stripped off because of cohesive failure, resulting in adhesive remaining. The property evaluation was hence impossible.

While the invention has been described in detail and with reference to specific embodiments thereof, it will be apparent to one skilled in the art that various changes and modifications can be made therein without departing from the scope thereof.

This application is based on Japanese patent application No. 2004-131809 filed Apr. 27, 2004, the entire contents thereof being hereby incorporated by reference.

What is claimed is:

1. A medical non-crosslinked pressure-sensitive adhesive composition which comprises an adhesive polymer A having a weight-average molecular weight of from 500,000 to 1,000,000, an adhesive polymer B having a weight-average molecular weight of from 1,000,000 to 1,500,000, and a liquid plasticizer, wherein the adhesive polymer A is a polymer obtained by copolymerizing one or more alkyl (meth)acrylates with N-vinyl-2-pyrrolidone and the adhesive polymer B is either a polymer obtained by the polymerization of one or more alkyl (meth)acrylates or a polymer obtained by copolymerizing one or more alkyl (meth)acrylates with one or more comonomers other than N-vinyl-2-pyrrolidone.

2. The medical non-crosslinked pressure-sensitive adhesive composition of claim 1, wherein the adhesive polymer B is an adhesive polymer prepared by the emulsion polymerization method.

3. The medical non-crosslinked pressure-sensitive adhesive composition of claim 1, wherein the adhesive polymer A and the adhesive polymer B each are a polymer obtained by polymerizing one or more monomers in which at least 50% by weight thereof is one or more alkyl (meth)acrylates having an alkyl group having from 4 to 12 carbon atoms as the ester side chain.

4. The medical non-crosslinked pressure-sensitive adhesive composition of claim 1, wherein the adhesive polymer A is a polymer obtained by copolymerization with from 10 to 50% by weight N-vinyl-2-pyrrolidone based on the polymer.

5. The medical non-crosslinked pressure-sensitive adhesive composition of claim 1, wherein the adhesive polymer A and the adhesive polymer B are contained in a ratio of from 1:4 to 4:1 by weight.

6. The medical non-crosslinked pressure-sensitive adhesive composition of claim 1, wherein the proportion of the liquid plasticizer is from 10 to 240 parts by weight per 100 parts by weight of the sum of the adhesive polymer A and the adhesive polymer B.

7. The medical non-crosslinked pressure-sensitive adhesive composition of claim 1, wherein the liquid plasticizer comprises a fatty acid ester formed from a monovalent saturated fatty acid having from 12 to 18 carbon atoms and a monohydric alcohol having from 1 to 8 carbon atoms.

8. A medical adhesive sheet which comprises a support and, formed on at least one side of the support, a layer of the medical non-crosslinked pressure-sensitive adhesive composition of claim 1.

9. The medical adhesive sheet of claim 8, which further comprises a percutaneously absorbable drug in the layer of the medical non-crosslinked pressure-sensitive adhesive composition.

10. A process for producing a medical non-crosslinked pressure-sensitive adhesive composition which comprises:
(a) polymerizing one or more alkyl (meth)acrylates by the emulsion polymerization method or copolymerizing one or more alkyl (meth)acrylates with one or more comonomers other than N-vinyl-2-pyrrolidone by the emulsion polymerization method to prepare a liquid containing a polymer having a weight-average molecular weight of from 1,000,000 to 1,500,000 as an adhesive polymer B;
(b) mixing a liquid plasticizer is mixed with the liquid prepared in (a) to thereby swell the adhesive polymer B; and
(c) mixing the liquid prepared in (b) with a liquid which contains an adhesive polymer A having a weight-average molecular weight of from 500,000 to 1,000,000 and has been separately prepared by copolymerizing one or more alkyl (meth)acrylates with N-vinyl-2-pyrrolidone by the solution polymerization method.

* * * * *